United States Patent
Bronson et al.

(10) Patent No.: US 9,332,879 B1
(45) Date of Patent: May 10, 2016

(54) COMBINATION GRINDER AND VAPORIZATION BOWL

(71) Applicants: Joseph A. Bronson, Aumsville, OR (US); Jareb Bronson, Aumsville, OR (US)

(72) Inventors: Joseph A. Bronson, Aumsville, OR (US); Jareb Bronson, Aumsville, OR (US)

(*) Notice: Subject to any disclaimer, the term of this patent is extended or adjusted under 35 U.S.C. 154(b) by 472 days.

(21) Appl. No.: 13/961,474

(22) Filed: Aug. 7, 2013

Related U.S. Application Data

(60) Provisional application No. 61/680,434, filed on Aug. 7, 2012.

(51) Int. Cl.
*A47J 42/00* (2006.01)
*A47J 42/14* (2006.01)
*A61M 11/04* (2006.01)
*B02C 18/08* (2006.01)
*A47J 42/34* (2006.01)

(52) U.S. Cl.
CPC *A47J 42/14* (2013.01); *A47J 42/34* (2013.01); *A61M 11/04* (2013.01); *A61M 11/041* (2013.01); *B02C 18/08* (2013.01)

(58) Field of Classification Search
CPC .... B02C 18/00; B02C 18/08; B02C 18/2216; B02C 19/04; B02C 19/06; A61M 11/04; A61M 11/041; A47J 42/14; A47J 42/24; A47J 42/00; A47J 42/34
USPC .......................... 241/168, 169.1, 273.3, 101.2
See application file for complete search history.

(56) References Cited

U.S. PATENT DOCUMENTS

| | | | |
|---|---|---|---|
| 3,705,415 A | 12/1972 | Katzman et al. | |
| 4,304,363 A | 12/1981 | Atkielski | |
| 6,513,524 B1 | 2/2003 | Storz | |
| 7,147,174 B2 * | 12/2006 | Mansen | B02C 13/22 241/169.1 |
| 7,367,519 B2 * | 5/2008 | de Groote | A47J 19/04 241/168 |
| 7,422,170 B2 | 9/2008 | Bao | |
| 7,886,999 B2 * | 2/2011 | Ruzycky | A47J 19/06 241/168 |
| 7,997,280 B2 * | 8/2011 | Rosenthal | A61M 11/041 128/202.21 |
| 8,393,563 B2 * | 3/2013 | Chaoui | B02C 18/08 241/168 |
| 8,613,402 B2 * | 12/2013 | Lefkovitz | A47J 19/06 241/100 |
| 8,695,906 B2 * | 4/2014 | Hainbach | A47J 42/14 241/169.1 |
| 2014/0060552 A1 * | 3/2014 | Cohen | A24F 47/008 131/273 |
| 2014/0373857 A1 * | 12/2014 | Steinberg | A24F 47/008 131/329 |
| 2015/0223523 A1 * | 8/2015 | McCullough | A61M 15/005 131/328 |

* cited by examiner

*Primary Examiner* — Faye Francis
(74) *Attorney, Agent, or Firm* — Robert C. Montgomery; Montgomery Patent & Design

(57) ABSTRACT

A vaporizer bowl having an integral internal grinding mechanism has a plurality of internal stainless steel prongs and is split in hemispherical halves. In use, a substance used to create a desired vapor is placed within the bowl. The prongs grind/cut the substance as the halves of the bowl are turned in opposing directions. Such action ensures that the substance is completely consumed, allowing for less waste or the use of less material.

17 Claims, 4 Drawing Sheets

COMBINATION GRINDER AND VAPORIZATION BOWL

RELATED APPLICATIONS

The present invention was first described in and claims the benefit of U.S. Provisional Application No. 61/680,434, filed Aug. 7, 2012, the entire disclosures of which are incorporated herein by reference.

FIELD OF THE INVENTION

The present invention relates to a grinding mechanism in two (2) components configured to be in fluid communication with a vaporizer, the grinding mechanism able to grind smokable substances into finer particles.

BACKGROUND OF THE INVENTION

Many people utilize an herbal vaporizer for the purposes of smoking herbal or tobacco products. The use of a vaporizer eliminates the production of irritating toxins normally associated with the smoking process in that there is no actual smoke being inhaled. An herbal vaporizer accomplishes this by heating the material to a specific temperature, which releases the desired active ingredients from the material, but without heating it to combustion. However, one (1) disadvantage of such units is that a quantity of the contained product will not be consumed due to its orientation and configuration inside of the unit. This material is then typically wasted and must be discarded thus wasting money. Any attempt at manual mixing exposes the product to rapidly changing temperatures as well as the user to possible burns. Accordingly, there exists a need for a means by which various products inside of vaporizer herbal vaporizers can be completely consumed in order to address the problems as described above.

Prior art in this field consists of grinder and mixing apparatuses used to grind and mix smoking substances before the substance is smoked. No art exists that provides the benefit of concurrently smoking a substance and grinding/mixing the substance within one (1) device. If prior art vaporizer bowels grants a user access to the substance held within at all, the configuration of these prior art force a user to employ burdensome and dangerous methods to grind/mix substances during smoking such substances. Other vaporizer bowl constructions prevent such mixing/grinding all-together. It is an objective of this invention to provide a means to smoke substances via a vaporizing method and to have the ability to grind/mix the substance held within. It is a further objective of this invention to achieve this in a safe and cost-effective manner by merely rotating the device with a user's hand. It is a further objective of this invention to provide a means to support the substance held within in an elevated posture to as to facilitate convectional flow through the substance. It is a further objective of this invention to employ these methods to fully and completely consume the substance being smoked so as to reduce waste and save costs to the user.

SUMMARY OF THE INVENTION

The device comprises a combination grinder and vaporizer bowl configured together to enable a user to grind a smoking substance without having to separately grind the substance prior to use. The device is provided with upper and lower compartments, each having hemispherical shapes. Each compartment is joined together by a lip disposed about a perimeter edge of each compartment. Extending from a top surface of the upper compartment is an exhaust tube that is specifically configured to facilitate attachment of various smoking accessories to enable a user to inhale volatiles emitted from smoldering substances held within Protruding from a lower surface of the lower compartment are a plurality of support legs to facilitate an up-right and elevated posture for the device. Disposed about a perimeter surface of each compartment are grips to enable a user to grasp each compartment and rotate each compartment independently. This feature is important to allow a user to grind the substance held within the device.

An interior of the device is provided with a screen to support substances in an elevated position with respect to a bottom inner surface of the lower compartment and facilitate conventional currents to pass through the substance. Each compartment is further provided with prongs protruding from an inner surface of each compartment. These prongs enable grinding and mixing of the substance held within when the compartments are rotated. Each prong is strategically positioned to obviate interference with each other when the compartments are rotated.

During use of the device, a user frequently rotates each compartment to allow for thorough mixing of the entire substance contained within. Such action ensures that the substance is completely consumed, allowing for less waste or the use of less material. The specific arrangement of the prongs ensures complete grinding and consumption. The use of the device provides for the vaporization of herbal products in a manner which is not only easy and effective, but quick and safe as well.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

Figure 1:
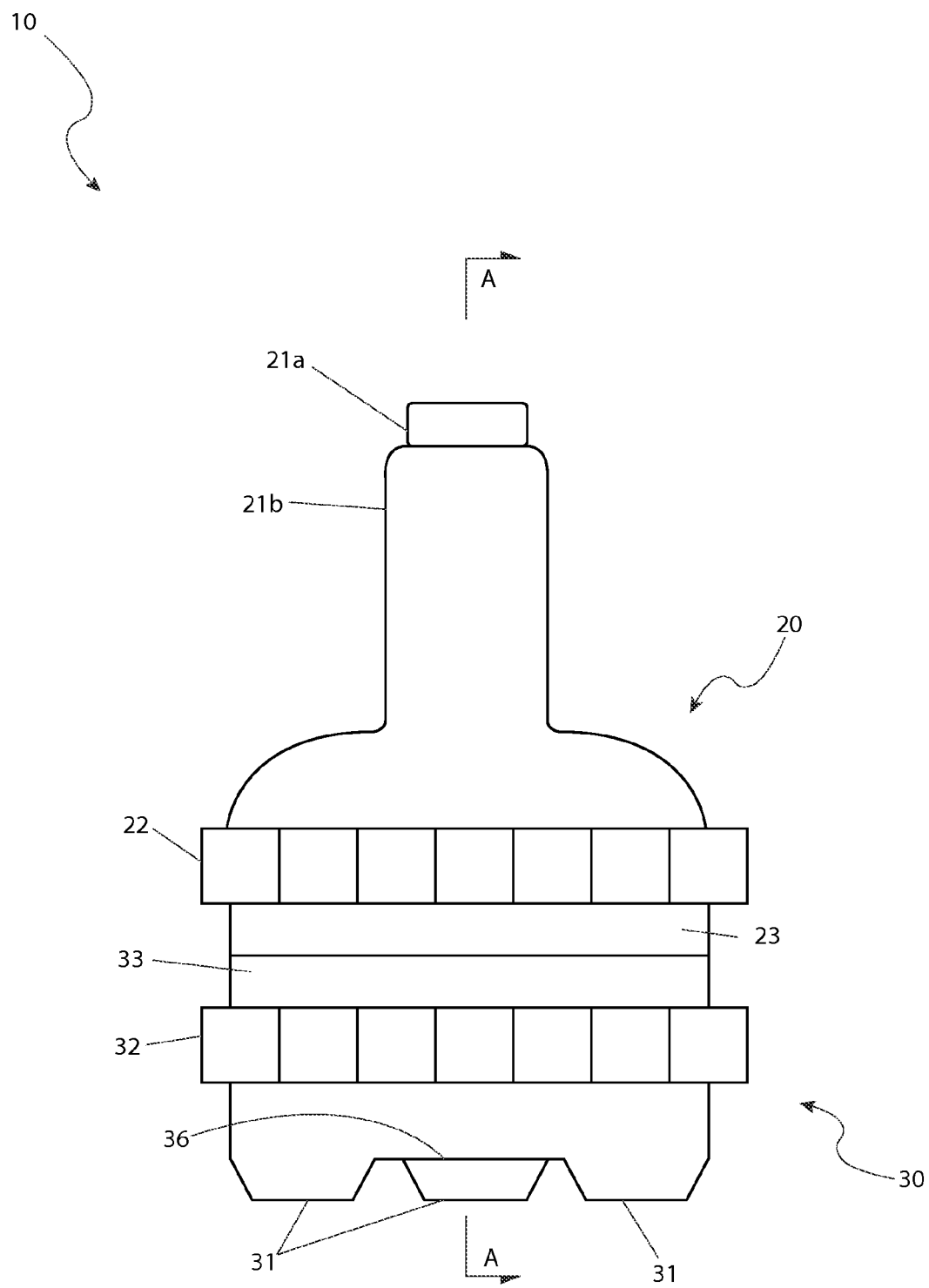
FIG. 1 is an elevation view of a combination grinder and vaporizer bowl 10, according to a preferred embodiment of the present invention.

DESCRIPTIVE KEY 10 combination grinder and vaporizer bowl
20 upper component
21a exhaust adapter
21b connector
22 upper grip
23 upper rim
24 exhaust aperture
25 substance
30 lower component
31 support legs
32 lower grip
33 lower rim
34a screen
34b screen shelf
35 prong aperture 36 lower opening
41a upper prongs
41b lower prongs
100 hot air
105 vapor

DETAILED DESCRIPTION OF THE PREFERRED EMBODIMENT

The best mode for carrying out the invention is presented in terms of its preferred embodiment, herein depicted within FIGS. 1 through 4. However, the invention is not limited to the described embodiment and a person skilled in the art will appreciate that many other embodiments of the invention are possible without deviating from the basic concept of the invention, and that any such work around will also fall under scope of this invention. It is envisioned that other styles and configurations of the present invention can be easily incorporated into the teachings of the present invention, and only one particular configuration shall be shown and described for purposes of clarity and disclosure and not by way of limitation of scope.

The terms "a" and "an" herein do not denote a limitation of quantity, but rather denote the presence of at least one of the referenced items.

The present invention describes a combination grinder and vaporizer bowl (herein described as the "apparatus") 10, which provides a means for grinding a substance 25 such as an organic product without having to separately grind the substance 25 prior to use in a vaporizer such as a volcano-style vaporizer.

Referring now to FIG. 1, an environmental view of the apparatus 10, according to the preferred embodiment of the present invention, is disclosed. The apparatus 10 comprises an upper component 20 and a lower component 30. Both components 20, 30 comprise generally hemispherical-shaped vessels. The components 20, 30 are envisioned to be manufactured from a durable and insulating plastic material. The upper component 20 and lower component 30 portions are joined by respective connecting upper rim 23 and lower rim 33 portions (see FIGS. 2 and 3). The diameter of the upper rim 23 is large enough to snugly encompass the diameter of the lower rim 33. As such, the upper component 20 is removably attachable to the lower component 30.

The upper component 20 comprises a hollow tubular exhaust adapter 21a which protrudes upwardly being designed to facilitate attachment of accessories of the existing vaporizer such as a bag or hose via a tubular connector portion 21b being press-fit or otherwise permanently attached to an upper end portion. The lower component 30 comprises a plurality of integrally-molded support legs 31 along its bottom surface. The support legs 31 enable the apparatus 10 to stand on any surface as well as enabling the apparatus 10 to be properly positioned within the vaporizer. The upper component 20 and the lower component 30 both comprise grips 22, 32 that enable each component 20, 30 to be manually held and operated. The grips 22, 32 completely encircle the components 20, 30 in a parallel manner, thereby allowing a user to grasp and turn said grips 22, 32 in opposing directions to grind the substance 25 deposited within (see FIG. 4).

Figure 2:
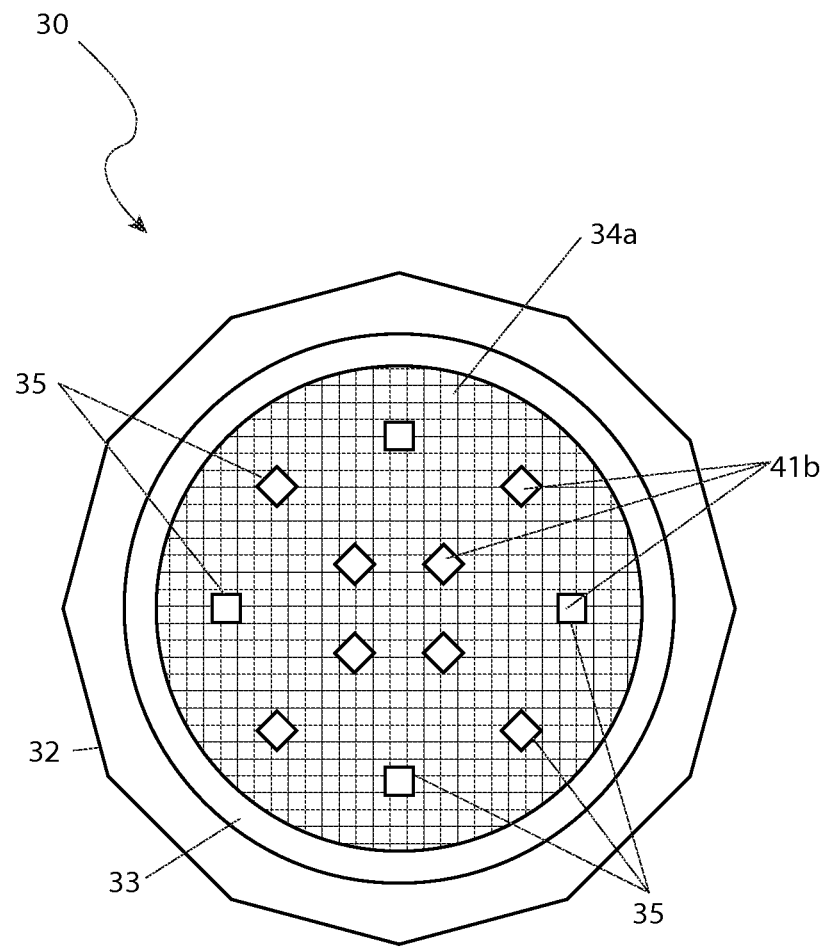
FIG. 2 is a top view of a lower component 30 of a combination grinder and vaporizer bowl 10, according to a preferred embodiment of the present invention.
Figure 3:
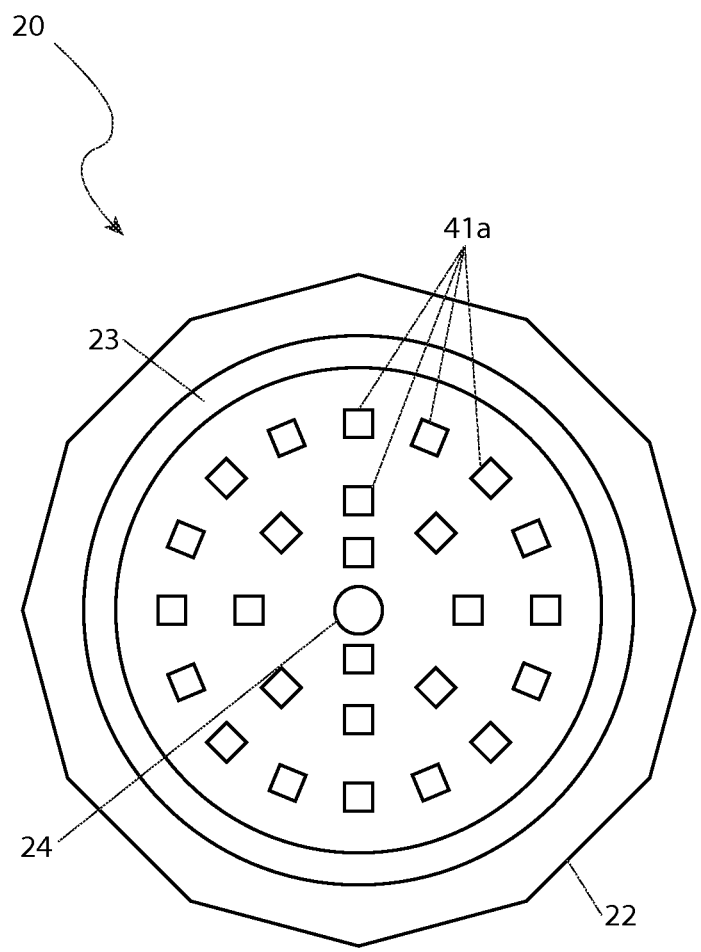
FIG. 3 is a bottom view of an upper component 20 of a combination grinder and vaporizer bowl 10, according to a preferred embodiment of the present invention; and, FIG. 4 is a sectional view of the combination grinder and vaporizer bowl 10 taken along section line A-A (see FIG. 1), according to a preferred embodiment of the present invention.

Referring now to FIGS. 2 and 3, an upper view of the lower component 30 and a lower view of the upper component 20, respectively, according to the preferred embodiment of the present invention, are disclosed. The lower component 30 comprises a removable screen 34 located horizontally within the lower compartment 30 spanning an inner space thereof, and resting upon a perimeter screen shelf 34b, positioned above a circular lower opening 36 being positioned between the support legs 31. The screen 34 supports an organic substance 25 placed into the apparatus 10, thereby positioning the substance 10 so as to allow hot air 100 from the vaporizer to flow through the lower opening 36 and vaporize oils within the substance 25 to produce a desired vapor 105.

The upper component 20 comprises an exhaust adapter 21b centrally located at an apex of the upper compartment 20 having an internal exhaust aperture 24 that enables the generated vapors created within the components 20, 30 to exit the exhaust adapter portion 21a of the apparatus 10. The upper component 20 and the lower component 30 comprise respective upper prongs 41a and lower prongs 41b. The prongs 41a, 41b comprise sharp edge portions to grind the substance 25 to provide more complete consumption thereof (see FIG. 4).

Figure 4:
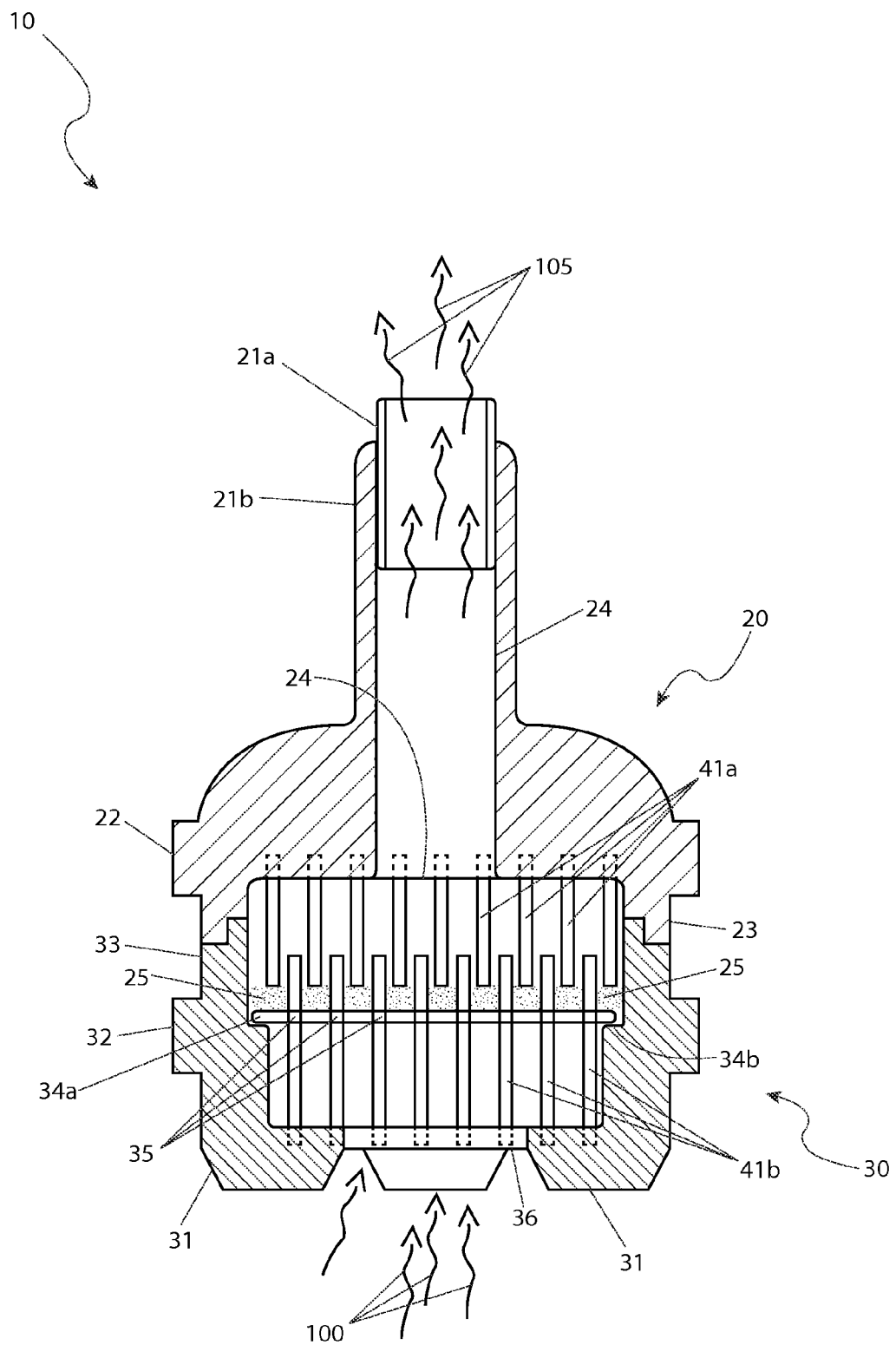

Referring now to FIG. 4, a sectional view of the apparatus 10 taken along section line A-A (see FIG. 1), according to a preferred embodiment of the present invention, is disclosed. The prongs 41a, 41b comprise rigid appendages being embedded or otherwise rigidly fastened to inner upper and inner lower surfaces of the upper 20 and lower 30 compartments, respectively. The prongs 41a, 41b comprise sharp edge portions. The prongs 41a, 41b are envisioned to have rectangular cross-sections, or another sharp-edged shape, and be made of a rigid and durable material, such as stainless steel. The upper prongs 41a and lower prongs 41b are arranged in corresponding circular patterns so as to not interfere with each other when the components 20, 30 are rotated; however, said prongs 41a, 41b provide minimal clearance therebetween when halves 20, 30 are joined so as to grind/cut the substance 25 from a large particle size to a smaller particle size. The lower prongs 41b are envisioned to be inserted through correspondingly sized and positioned prong apertures 35 formed in the screen 34. The grinding of the substance 25 takes place by rotating the upper component 20 and the lower component 30 in opposing directions by utilizing the upper grip 22 and lower grip 32 portions.

It is envisioned that other styles and configurations of the present invention can be easily incorporated into the teachings of the present invention, and only one particular configuration shall be shown and described for purposes of clarity and disclosure and not by way of limitation of scope.

The preferred embodiment of the present invention can be utilized by the common user in a simple and effortless manner with little or no training. After initial purchase or acquisition of the apparatus 10, it would be installed as indicated in FIG. 1.

The method of utilizing the apparatus 10 may be achieved by performing the following steps: procuring a model of the apparatus 10 that is of a corresponding size and configuration to fit within a particular existing vaporizer model; placing the screen 34 into the lower component 30; placing a quantity of the substance 25, such as an herbal and/or organic product, onto the screen 34; attaching the upper component 20 onto the lower component 30; grinding the substance 25 by rotating the upper compartment 20 and lower compartment 30 in opposing directions using the grips 22, 32; installing the apparatus 10 into the vaporizer; attaching any desired vaporizer accessories such as an exhaust bag onto the exhaust connector 21b; activating the vaporizer in a normal manner; allowing hot air 100 from the vaporizer to flow up into the lower component 30 and through the substance 25, causing the now treated vapors 105 to flow upward out of the upper component portion 20 of the device 10; and, saving time and effort preparing a vaporizer without having to grind the substance portion 25 in a separate grinding process while using the present invention 10.

The foregoing descriptions of specific embodiments of the present invention have been presented for purposes of illustration and description. They are not intended to be exhaustive or to limit the invention and method of use to the precise forms disclosed. Obviously many modifications and variations are possible in light of the above teaching. The embodiment was chosen and described in order to best explain the principles of the invention and its practical application, and to thereby enable others skilled in the art to best utilize the invention and various embodiments with various modifications as are suited to the particular use contemplated. It is understood that various omissions or substitutions of equivalents are contemplated as circumstance may suggest or render expedient, but is intended to cover the application or implementation without departing from the spirit or scope of the claims of the present invention.

What is claimed is:

1. A grinder system, comprising:
   a first component, having a first outer surface, an open first outer end providing access to a first inner portion, a first rim portion circumferentially located about a perimeter of said first outer end, and an exhaust adapter extending outwardly from said first outer surface opposite said first outer end and in fluid communication with said first inner portion;
   a second component, having a second outer surface, an open second outer end providing access to a second inner portion, and a second rim portion circumferentially located about a perimeter of said second outer end;
   a first grinding mechanism located within said first inner portion and extending towards said first outer end; and,
   a second grinding mechanism located within said second inner portion and extending towards said second outer end;
   wherein said first rim portion correspondingly mates with said second rim portion to conjoin said first component to said second component;
   wherein said exhaust adapter is configured to attach the grinder system to a vaporizer; and,
   wherein said first and second grinding mechanisms are configured to grind a substance into fine particles when said first and second components are conjoined.

2. The grinder system of claim 1, wherein said first component half and second component each comprise a generally hemispherical-shaped vessel.

3. The grinder system of claim 1, further comprising a plurality of support legs located on said second outer surface opposite said second outer end.

4. The grinder system of claim 3, wherein said plurality of support legs are each a molded integral portion of said second outer surface.

5. The grinder system of claim 1, further comprising a shelf circumferentially located about an inner perimeter of said second inner portion, subjacent from said second outer end.

6. The grinder system of claim 5, further comprising a removable screen adapted to be placed on said second inner portion and resting on said shelf;
   wherein said removable screen spans a width of said second inner surface; and,
   wherein said removable screen permits passage of said second grinding mechanism therethrough.

7. The grinder system of claim 1, wherein:
   said first grinding mechanism comprises a plurality of first prongs, each having a sharpened edge portion and further having a first end attached to an inner surface of said first component opposite said first outer end; and,
   said second grinding mechanism comprises a plurality of second prongs, each having a sharpened edge portion and further having a first end attached to an inner surface of said second component opposite said second outer end.

8. The grinder system of claim 7, wherein said plurality of first prongs are arranged in a circular pattern on said first compartment and said plurality of second prongs are arranged in a circular pattern on said second compartment such that there is a minimal clearance therebetween when said first component and second component are conjoined.

9. A grinder system, comprising:
   a first component, having a first outer surface with a first grip, an open first outer end providing access to a first inner portion, a first rim portion circumferentially located about a perimeter of said first outer end, and an exhaust adapter extending outwardly from said first outer surface opposite said first outer end and in fluid communication with said first inner portion;
   a second component, having a second outer surface with a second grip, an open second outer end providing access to a second inner portion, and a second rim portion circumferentially located about a perimeter of said second outer end;
   a first grinding mechanism located within said first inner portion and extending towards said first outer end; and,
   a second grinding mechanism located within said second inner portion and extending towards said second outer end;
   wherein said first rim portion correspondingly mates with said second rim portion to conjoin said first component to said second component;
   wherein said exhaust adapter is configured to facilitate attachment to a vaporizer; and,
   wherein said first and second grinding mechanisms are configured to grind a substance into fine particles when said first and second components are conjoined.

10. The grinder system of claim 9, wherein said first component half and second component each comprise a generally hemispherical-shaped vessel.

11. The grinder system of claim 9, further comprising a plurality of support legs located on said second outer surface opposite said second outer end.

12. The grinder system of claim 11, wherein said plurality of support legs are each a molded integral portion of said second outer surface.

13. The grinder system of claim 9, wherein:
   said first grip is circumferentially located on said first outer surface; and,
   said second grip is circumferentially located on said second outer surface.

14. The grinder system of claim 9, further comprising a shelf circumferentially located about an inner perimeter of said second inner portion, subjacent from said second outer end.

15. The grinder system of claim 14, further comprising a removable screen adapted to be placed on said second inner portion and resting on said shelf;
   wherein said removable screen spans a width of said second inner surface; and,
   wherein said removable screen permits passage of said second grinding mechanism therethrough.

16. The grinder system of claim 9, wherein:
   said first grinding mechanism comprises a plurality of first prongs, each having a sharpened edge portion and further having a first end attached to an inner surface of said first component opposite said first outer end; and, said second grinding mechanism comprises a plurality of second prongs, each having a sharpened edge portion and further having a first end attached to an inner surface of said second component opposite said second outer end.

17. The grinder system of claim 16, wherein said plurality of first prongs are arranged in a circular pattern on said first compartment and said plurality of second prongs are arranged in a circular pattern on said second compartment such that there is a minimal clearance therebetween when said first component and second component are conjoined.

* * * * *